(12) United States Patent
Saitoh et al.

(10) Patent No.: US 7,957,636 B2
(45) Date of Patent: Jun. 7, 2011

(54) ILLUMINATION APPARATUS AND APPEARANCE INSPECTION APPARATUS INCLUDING THE SAME

(75) Inventors: Kenji Saitoh, Atsugi (JP); Hiroshi Yoshikawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/612,601

(22) Filed: Nov. 4, 2009

(65) Prior Publication Data

US 2010/0111515 A1    May 6, 2010

(30) Foreign Application Priority Data

Nov. 5, 2008   (JP) .................................. 2008-284223

(51) Int. Cl.
G03B 15/03 (2006.01)
(52) U.S. Cl. ...................................................... 396/155
(58) Field of Classification Search ................... 396/155
See application file for complete search history.

(56) References Cited

U.S. PATENT DOCUMENTS 5,117,249 A * 5/1992 Spector ............................ 396/3
2007/0292088 A1 12/2007 Saitoh

FOREIGN PATENT DOCUMENTS

| JP | 2000-315256 A | 11/2000 |
| JP | 2004-194689 A | 7/2004 |
| JP | 2007-334216 A | 12/2007 |

* cited by examiner

*Primary Examiner* — Rodney E Fuller
(74) *Attorney, Agent, or Firm* — Canon U.S.A., Inc., IP Division

(57) ABSTRACT

An illumination apparatus which illuminates a surface of an object having a three-dimensional shape includes a light source, a guide configured to guide light from the light source to a surface of the object, and a diffuser which has a diffusion-reflection surface that faces a light exit surface of the guide via the object, wherein the diffuser is arranged at such a position that the light which is emitted from the guide and is not directly incident on the object is incident on the diffusion-reflection surface while a part of the light reflected and diffused by the diffusion-reflection surface is incident on a surface of the object.

6 Claims, 13 Drawing Sheets

ILLUMINATION APPARATUS AND APPEARANCE INSPECTION APPARATUS INCLUDING THE SAME

BACKGROUND OF THE INVENTION

1. Field of the Invention

The present invention relates to an illumination apparatus useful for inspecting a surface of an object which has a three-dimensional shape, for example, a cylindrical shape to detect presence of a defect such as a surface flaw or a dent/projection or non-uniformity of the surface, and an appearance inspection apparatus which includes such an illumination apparatus.

2. Description of the Related Art

Various appearance inspection apparatuses (object surface inspection apparatuses) that are used for detecting presence of a surface defect, such as a flaw, a dent/projection, and adhesion of a foreign substance, of an object to be inspected has been proposed.

As an appearance inspection apparatus, for example, an inspection apparatus is known that irradiates a surface of an object to be inspected with uniform projection light and detects its surface defect based on obtained distribution of light (or its image), which is composed of specular reflection light and diffused reflection light from the surface of the object.

Japanese Patent Application Laid-Open No. 2007-334216 (US 2007/0292088) discusses an appearance inspection apparatus that efficiently evaluates an uneven surface state of an object to be inspected caused by distribution of surface dents and projections.

It is conventionally known that by using tangential illumination light which is provided close to the surface and incident on the surface at an angle of approximately 90 degrees, the surface state of the object can be accurately detected without being affected by microstructure of the object at the surface. This method is especially effective in detecting a foreign substance or a dust attached to the surface.

Japanese Patent Application Laid-Open No. 2004-194689 and Japanese Patent Application No. 2000-315256 discuss an apparatus that inspects appearance of an object which has a curved inspection surface rather than a flat surface.

When carrying out appearance inspection of a surface of an object, it is important to efficiently evaluate the uneven surface state caused by the distribution of surface dents and projections, a dust or a foreign substance attached to the surface, and surface roughness (hereinafter collectively called as "surface defect").

Generally, when a surface defect is inspected using an image of an inspection surface, the surface defect can be accurately and easily detected (observed) under an optimum lighting condition that is changed according to a type of the surface defect, for example, if the inspection surface is uniformly illuminated with light and an incident angle of the light with respect to the inspection surface is large.

In order to accurately inspect a surface defect of an object which has a three-dimensional shape such as a cylindrical object or a spherical object, it is important to efficiently illuminate the inspection surface with light of even light distribution and of a large incident angle.

However, it has been difficult for the conventional illumination apparatus to illuminate a surface of a three-dimensional shape object under a lighting condition that is adjusted according to a type of the surface defect.

More particularly, it has been very difficult to efficiently inspect different types of surface defects without being affected by a surface structure of the inspected object having a three-dimensional shape.

SUMMARY OF THE INVENTION

The present invention is directed to an illumination apparatus that can illuminate a surface of an object to be inspected for detecting a surface defect, in other words, various surface defects on a surface of an illuminated object with light using good lighting condition so that the inspection can be easily performed without being affected by structure of the surface.

According to an aspect of the present invention, an illumination apparatus which illuminates a surface of an object having a three-dimensional shape includes a light source, a guide configured to guide light from the light source to a surface of the object, and a diffuser which has a diffusion-reflection surface that faces a light exit surface of the guide via the object, wherein the diffuser is arranged at such a position that the light which is emitted from the guide and is not directly incident on the object is incident on the diffusion-reflection surface while a part of the light reflected and diffused by the diffusion-reflection surface is incident on a surface of the object.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

An illumination apparatus according to the present invention is useful for inspecting a surface of an object having a cylindrical shape. More particularly, the illumination apparatus is useful for inspecting a photosensitive drum for electrophotography and a fixing roller of a fixing apparatus which are used, for example, in an image output apparatus such as a copier or a laser printer.

The illumination apparatus and an appearance inspection apparatus including the illumination apparatus as exemplary embodiments according to the present invention will be described referring to the drawings. With respect to each drawing, a same member will be given a same reference number and descriptions of the members that overlap will be omitted.

First, an appropriate configuration for evaluating an uneven surface state (illumination state) that is caused by distribution of surface dents and projections of the object to be inspected will be described according to a first exemplary embodiment of the present invention.

Figure 1:
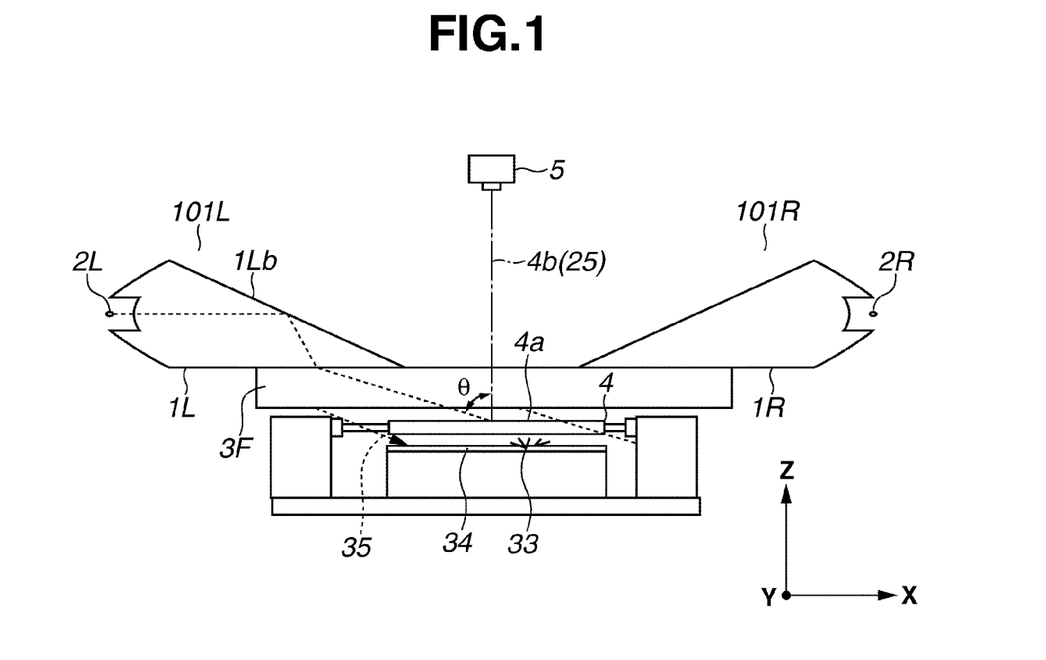
FIG. 1 is a lateral view of a main portion of an appearance inspection apparatus according to a first exemplary embodiment of the present invention.

FIG. 1 is a lateral view of a main portion of an appearance inspection apparatus used for evaluating an uneven surface state caused by the distribution of the surface dent/projection of the object to be inspected according to the first exemplary embodiment of the present invention.

Figure 2:
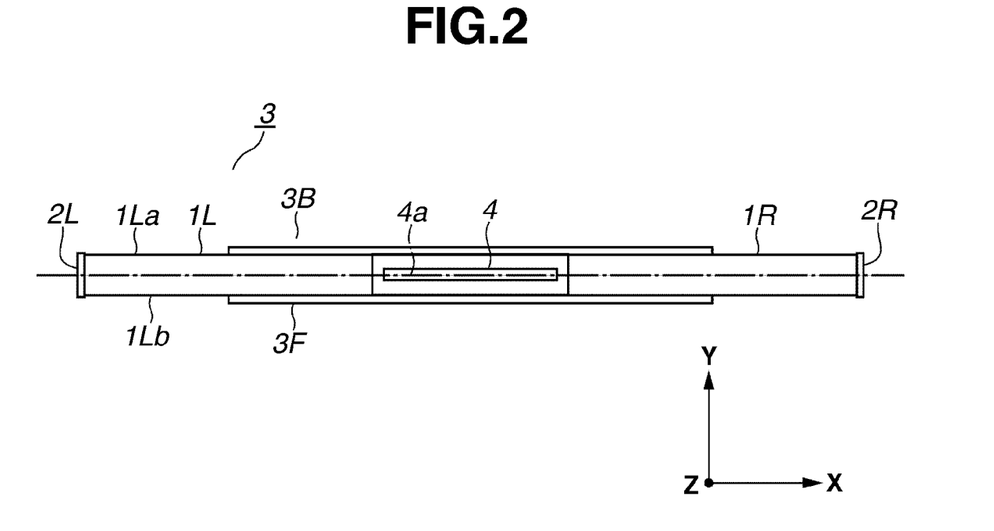
FIG. 2 is a top view of the main portion of the appearance inspection apparatus according to the first exemplary embodiment of the present invention.
Figure 3:
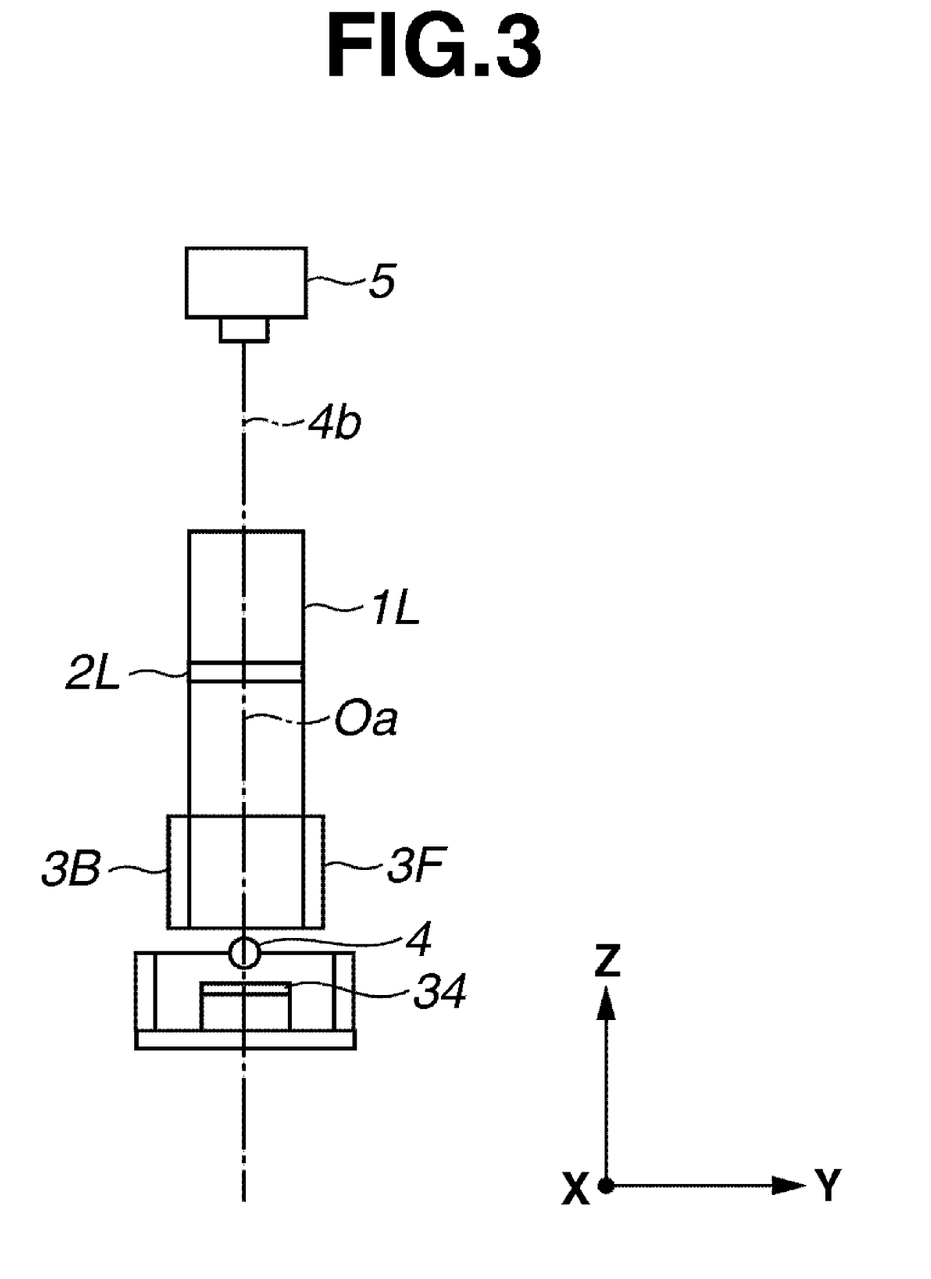
FIG. 3 is a front view of the main portion of the appearance inspection apparatus according to the first exemplary embodiment of the present invention.

FIG. 2 is a top view of the main portion and FIG. 3 is a front view of the main portion of the appearance inspection apparatus illustrated in FIG. 1.

The appearance inspection apparatus according to the present exemplary embodiment includes an illumination apparatus used for illuminating an inspection surface of an object to be inspected and a camera used for taking an image of the inspection surface.

FIGS. 1 to 3 illustrate illumination apparatuses 101L and 101R. The illumination apparatuses 101L and 101R may be collectively referred to as an illumination apparatus 101 in the description below. Each of prism members 1L and 1R includes a light incident surface and a light reflection surface. The prism members 1L and 1R may be collectively referred to as a prism member 1 in the description below.

Light sources 2L and 2R are correspondingly arranged to the prism members 1L and 1R. The light sources 2L and 2R may be collectively referred to as a light source 2 in the description below. Each of mirrors 3F and 3B includes a reflection surface that is arranged along a longitudinal direction of the inspection surface. The reflection surfaces of the mirrors 3F and 3B face each other with an object 4 to be inspected therebetween. The mirrors 3F and 3B may be collectively referred to as a reflection member 3 in the description below. If the object to be inspected is cylindrical, the mirrors 3F and 3B will be arranged along a direction of a cylinder axis and facing each other.

The object 4 has a three-dimensional shape such as a rectangular parallelepiped or a cylinder. An inspection surface (illuminated surface) 4a, which is a portion of the object 4, is illuminated with the light emitted from the illumination apparatus 101. A camera 5 is used for taking an image of a portion of the inspection surface 4a of the object 4 that is illuminated with the light emitted from the illumination apparatus 101.

Each of the prism members 1L and 1R is a guide that guides a light flux which is emitted from the light sources 2L and 2R to the inspection surface of the object 4.

Considering viewability, the camera 5 illustrated in FIG. 1 is not illustrated in the top view of the appearance inspection apparatus in FIG. 2. The front view of the appearance inspection apparatus illustrated in FIG. 3 is a diagrammatic sketch of the appearance inspection apparatus when it is viewed from the side of the light source 2L illustrated in FIG. 1.

In FIG. 1, a diffuser 34 which reflects and diffuses the incident light has a planar reflection-diffusion surface. The diffuser 34 is arranged on an opposite side of the prism member 1 with the object 4 therebetween. In other words, the diffuser 34 is arranged so that its diffusion-reflection surface faces the light exit surface of the prism member 1. The diffuser 34 is rectangular and is long in the longitudinal direction of the rectangular light flux that is emitted from the prism member 1.

Figure 7:
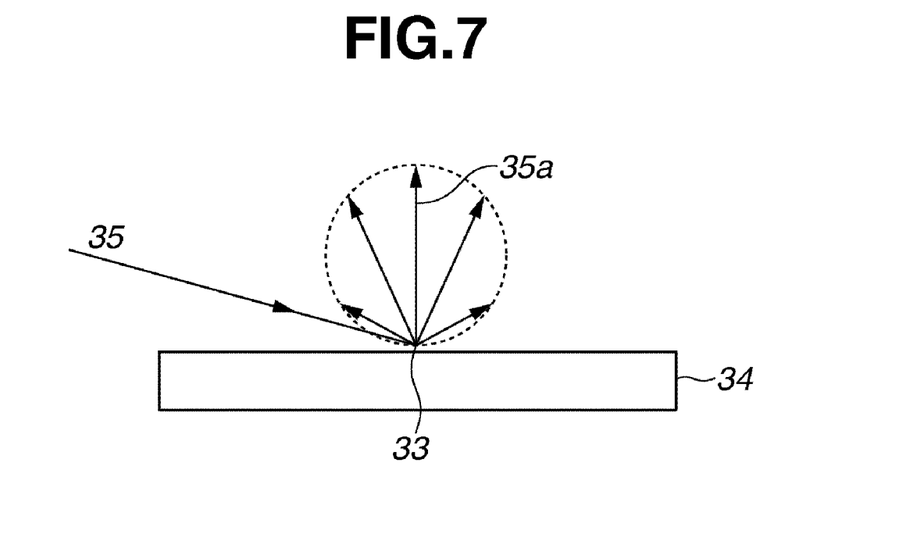
FIG. 7 illustrates a secondary diffused light source according to the first exemplary embodiment of the present invention.

FIG. 7 illustrates the diffuser 34. Among the light that is emitted from the prism member 1, an incident light 35 which passes in front of, behind, and the sides of the object 4 rather than being directly incident on the object 4, is incident on the diffuser 34.

A secondary diffused light source 33 is formed according to the incident light 35 that is incident on the diffuser 34.

FIG. 7 illustrates diffused light 35a that is diffused in various directions. The incident light 35 is directed onto the diffuser 34 and reflected and diffused at the position of the secondary diffused light source 33 on the diffuser 34. If the surface of the diffuser 34 is close to a perfect diffusion surface, intensity of the light does not substantially depend on the direction of the incident light. In other words, as illustrated in FIG. 7, the light will be the diffused light 35a that exhibits certain isotropic distribution.

According to the present exemplary embodiment, the inspection surface 4a of the object 4 is illuminated with the light emitted from the illumination apparatuses 101L and 101R. Then, an image of the inspection surface 4a is taken by the camera 5. The image is used for detecting a surface state such as presence of an adhering substance and a defect on the inspection surface 4a.

Further, according to the first exemplary embodiment, in order to realize uniform light quantity and light quantity distribution in the illumination area of the object 4, the illumination apparatus 101L that includes the prism member 1L and the light source 2L is arranged on the left side of the object 4. Furthermore, the illumination apparatus 101R having a similar configuration is arranged on the right side of the object 4.

Additionally, the lateral surface of the object 4 is illuminated with the diffused light 35a that is reflected and diffused by the diffuser 34.

According to the present exemplary embodiment, a cylindrical light-emitting tube is desirable to be used for the light sources 2L and 2R. However, a light source having a spherical light-emitting surface may also be used according to a shape of the prism members (light guide optical systems) 1L and 1R.

Although a xenon tube and a fluorescent light can be used as the cylindrical light-emitting tube, a xenon tube for a flash unit is more suitable.

Further, as the light source having a spherical light-emitting surface, for example, an incandescent lamp, a light-emitting diode (LED), and a halogen lamp can be used.

As the camera 5, an area sensor such as a charge-coupled device (CCD) or a complementary metal oxide semiconductor (CMOS) sensor can be used. Further, a digital camera or a video camera including a line sensor can also be used.

According to the first exemplary embodiment, the camera 5 is arranged such that its imaging axis (optical axis) 25 is in the vertical direction with respect to the inspection surface 4a of the object 4. The inspection surface 4a can be considered as one planar surface as a whole. A normal line 4b is a normal line of the inspection surface 4a. Thus, the imaging axis 25 matches the normal line 4b of the inspection surface 4a.

Since a refraction member such as a prism that may cause aberration is not provided between the camera 5 and the inspection surface 4a, a good image without aberration can be obtained.

The illumination apparatuses 101L and 101R illuminate the inspection surface 4a with the light from an oblique direction with respect to the normal line 4b. Since the illumination light is obliquely incident on the inspection surface 4a, the camera 5 takes an image of the object 4 using diffused reflection light from the inspection surface 4a. Thus, the image obtained by the camera 5 is a dark field image.

However, the appearance inspection apparatus according to the present exemplary embodiment is not limited to an apparatus that is capable of taking a dark field image. By arranging the angle of the camera 5 so that it is symmetrical with the incident angle of the illumination, a bright field image can also be taken using specular reflection light from the inspection surface 4a.

Figure 4A:
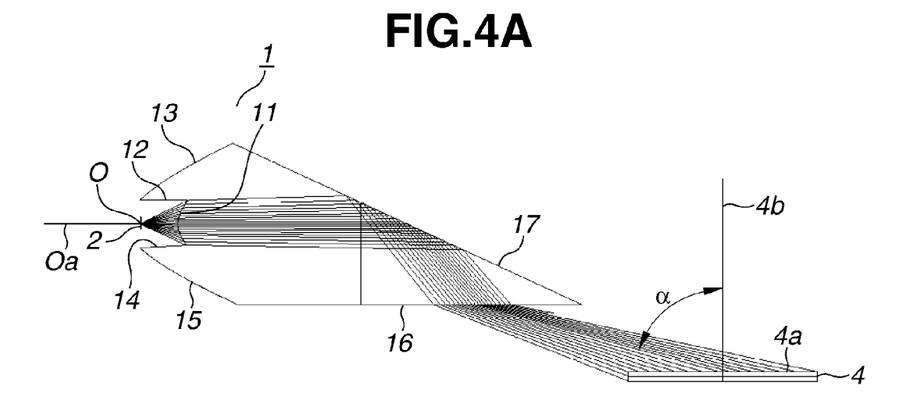
FIGS. 4A to 4C illustrate enlarged lateral views of a prism illustrated in FIG. 1 and results obtained from ray tracing.
Figure 4B:
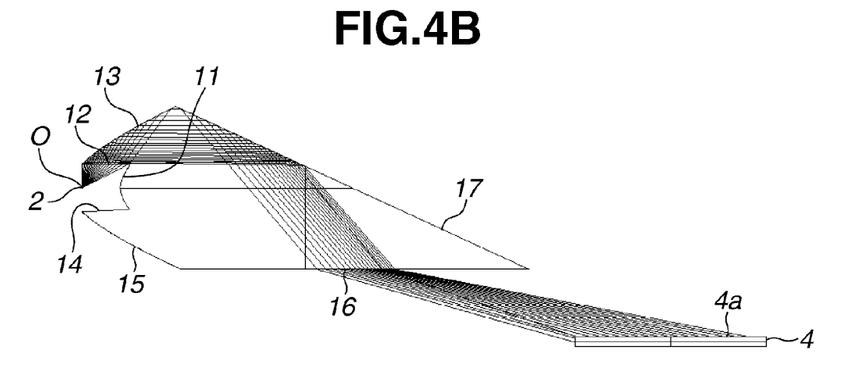
Figure 4C:
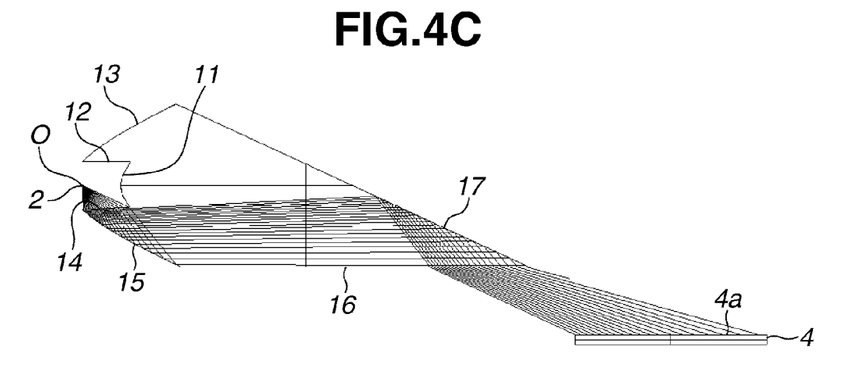

Each of FIGS. 4A, 4B, and 4C illustrates an enlarged view of a lateral surface of the prism member 1 and the object 4, and also a result of ray tracing of the light emitted from the light source 2.

The prism member 1 has a first light incident surface 11, a second light incident surface 12, a third light incident surface 14, a first reflection surface 17, a second reflection surface 13, a third reflection surface 15, and an exit surface 16.

The first light incident surface 11 is curved so as to have a light condensing function. The light that is incident on the first reflection surface 17, the second reflection surface 13, and the third reflection surface 15 is totally reflected. Further, these reflection surfaces may be formed as reflection surface with a metal film.

As illustrated in FIG. 4A, among the light fluxes that are emitted from a luminous point O of the light source 2, light fluxes that travel along an emitted light axis Oa and its vicinity in an axial direction thereof are directed onto the first light incident surface 11, reflected by the first reflection surface 17, and emitted from the exit surface 16.

On the other hand, as illustrated in FIG. 4B, among the light fluxes that are emitted from the luminous point O, light flux that is emitted above the emitted light axis Oa at a large angle with respect to the emitted light axis Oa and travels in a direction other than the axial direction is incident on the second light incident surface 12. At the second reflection surface 13 (the total reflection surface), the light flux is totally reflected in the first reflection surface direction. Then, the light flux is reflected by the first reflection surface 17 and emitted from the exit surface 16 in the direction of the illuminated surface.

Further, as illustrated in FIG. 4C, among the light fluxes that are emitted from the luminous point O, light flux that is emitted below the emitted light axis Oa at a large angle with respect to the emitted light axis Oa is incident on the third light incident surface 14. The light flux is totally reflected at the third reflection surface 15 (the total reflection surface). Then, the light flux is reflected by the first reflection surface 17 and emitted from the exit surface 16.

All the light fluxes that are emitted from the luminous point O are totally reflected by the first reflection surface 17, deflected, and emitted from the exit surface 16. Accordingly, the light fluxes illuminate the inspection surface 4a of the object 4 from an oblique direction.

By using the prism members 1L and 1R with the above described shape, the inspection surface 4a is efficiently illuminated with the light fluxes that are emitted in the forward direction (the side of the object 4) from the light source 2 using refraction and total reflection.

In the light that is incident on the first light incident surface 11, some light is not reflected and are directly emitted from the exit surface 16.

Further, in the light that is reflected by the second reflection surface 13 or the third reflection surface 15, some light is directly emitted from the exit surface 16.

The light ray that travels along the emitted light axis Oa and exits from the exit surface 16 of the prism member 1 is incident on the object 4 at an incident angle α. The incident angle α is set as 75°±10° (65°<θ<85°).

This is because, when a surface defect, such as a flaw or a dust, of an object is detected by using a dark field image, detection sensitivity can be improved by making the incident angle greater.

As illustrated in FIGS. 1 to 3, the mirrors 3F and 3B are provided between the exit surface 16 of the prism member 1 and the object 4. The mirrors 3F and 3B are parallel to an illumination reference plane (XZ plane) and face each other with the emitted light axis Oa therebetween. In other words, the mirrors 3F and 3B are provided in the longitudinal direction of the inspection surface 4a or in the direction of the cylinder axis if the object is cylindrical.

Further, as illustrated in FIG. 2, the mirrors 3F and 3B are arranged so that they are parallel to extension surfaces of lateral surfaces 1La and 1Lb of the prism member 1. In other words, the lateral surfaces 1La and 1Lb are arranged to be parallel to the XZ plane.

According to the above described configuration, light which is emitted from the exit surface 16 of the prism member 1 and travels in the lateral direction (Y direction) of the prism member 1, in other words, light that is emitted so that it has a component of a vertical direction with respect to the longitudinal direction (illumination reference plane (XZ plane)) of the inspection surface 4a is reflected in the direction of the inspection surface 4a.

Since the light that is emitted from the exit surface 16 are reflected by the mirrors 3F and 3B, the light fluxes that are incident on the inspection surface 4a of the object 4 increase, and efficient illumination can be achieved accordingly. Further, uniformity of light quantity distribution can be improved on the surface of the object 4 in the longitudinal direction and the lateral surface direction.

Figure 8:
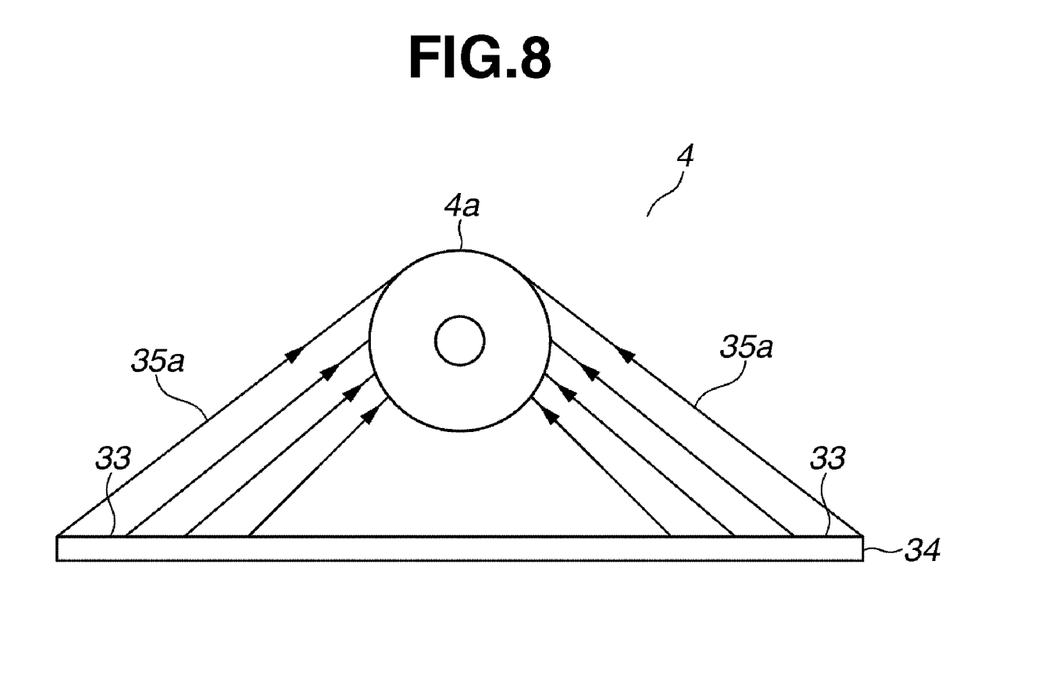
FIG. 8 illustrates light diffused by the secondary diffused light source according to the first exemplary embodiment of the present invention.

FIG. 8 illustrates an optical path of the diffused light 35a diffused from the secondary diffused light source 33 of the diffuser 34 when it illuminates the object 4. The diffused light 35a illuminates the inspection surface (cylindrical surface) 4a of the object 4 from an oblique direction.

If the three-dimensional object is cylindrical, the inspection surface 4a is illuminated with line illumination that is parallel to the cylinder axis of the object.

According to the present exemplary embodiment, the three-dimensional object is illuminated with the light which is emitted from the prism member 1 and include a considerable amount of oblique components. Further, a diffuser having a predetermined shape is set at a portion of the optical path of light that failed to illuminate the object, and the object is illuminated with the diffused light that is scattered by the secondary diffused light source. In this way, in addition to the light that includes a considerable amount of oblique components, the light that is emitted under different lighting conditions is simultaneously directed onto the object.

Next, illumination that is suitable for evaluating a surface state such as an adhering foreign substance or a surface roughness on a plane 21 which is a portion of the inspection surface 4a according to the present exemplary embodiment will be described referring to FIG. 5.

Figure 5:
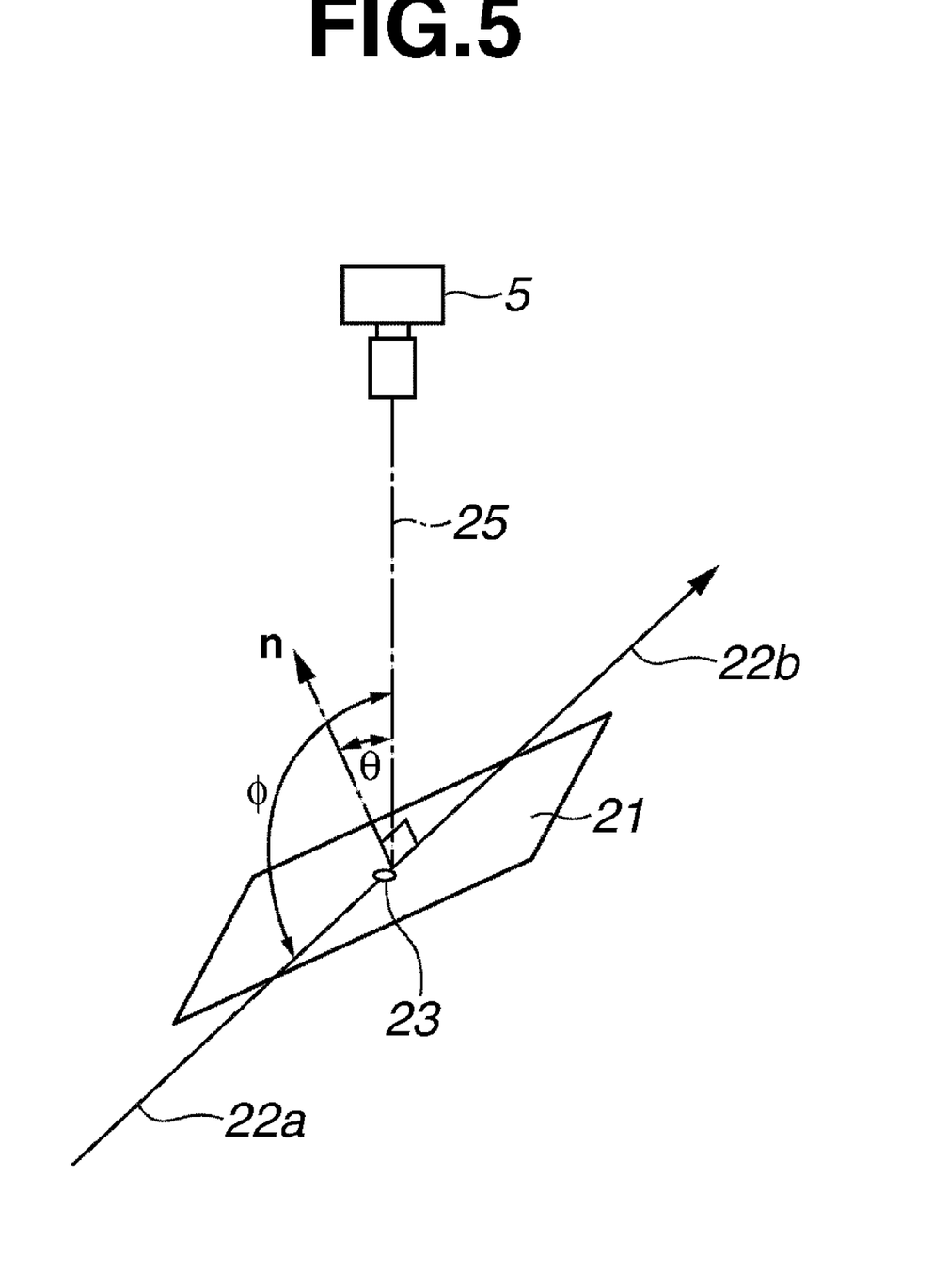
FIG. 5 illustrates a basic concept of an illumination system according to the first exemplary embodiment of the present invention.

FIG. 5 illustrates a first basic concept of the illumination that is suitable for evaluating an adhering substance 23 on a surface of the plane 21 of an extremely small area on the inspection surface 4a.

A surface of a three-dimensional object to be inspected that is cylindrical can be approximated by the plane 21 that is inclined at a certain angle if a vicinity of a predetermined location is considered. The plane 21 of the extremely small area has a normal line direction n. A light ray 22a is incident on the plane 21.

Emitted light ray 22b is a specular reflection of the light ray 22a from the plane 21. An angle θ is formed between the normal line n and the imaging axis 25 of the camera 5. Further, an angle φ is formed between the imaging axis 25 and the light ray 22a.

According to the present exemplary embodiment, an angle between the imaging axis 25 of the camera 5 and the direction of the emitted light ray 22b is set to be 90° or greater. Under such conditions, imaging using backscattering light is performed. At that time, light components that scattered into the normal line direction n are not incident on the camera 5.

By actively using the backscattering light, an image that is sensitive to the adhering substance 23, such as a foreign substance or a roughness, which is on the inspection surface 4a and highly likely to scatter the light can be obtained.

The imaging axis 25 does not match the normal line direction n. Accordingly, the image plane of the camera 5 is inclined and it is generally difficult to adjust focus on the whole image plane. For this reason, an image blur due to the inclination of the image plane is set at a detectable value in a range necessary for setting an F number (F no) of the camera 5, optimizing a focus position, and resolution of the foreign substance or surface roughness.

If it is directed to evaluation of the presence or size of the adhering substance 23 such as the foreign substance or surface roughness rather than obtaining structure thereof, the presence or size can be evaluated even if the image is defocused to some degree.

If a quantity of the light that is scattered due to the above-described foreign substance or surface roughness is evaluated, then it can be determined whether the foreign substance or the surface roughness is assumed to cause a problem.

According to the present exemplary embodiment, setting of a focal plane is determined from the overall configuration in order to obtain the most effective image when the focus is adjusted.

Figure 6:
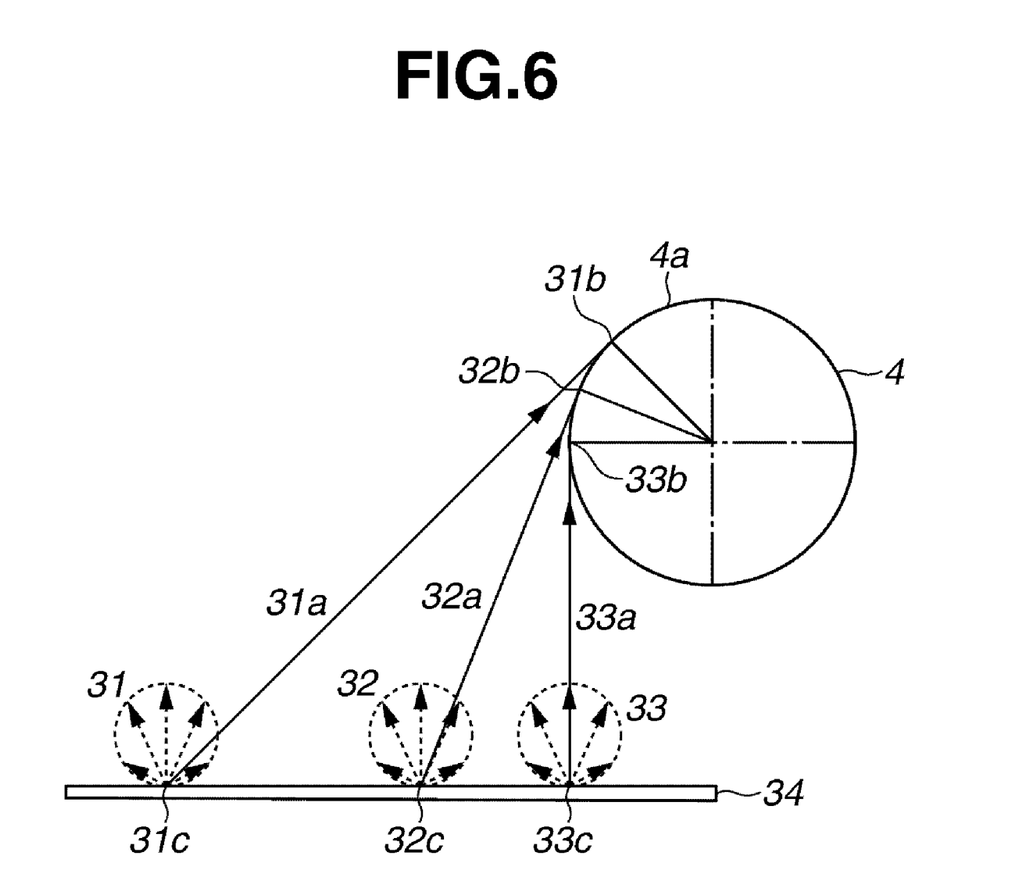
FIG. 6 illustrates a concept of the illumination system according to the first exemplary embodiment of the present invention.

FIG. 6 illustrates a concept of an appropriate illumination for evaluating an angle of the foreign substance attached to the surface of the object according to the first exemplary embodiment. Diffused light 31, 32, and 33 illustrate the light that is diffused from secondary diffused light sources 31c, 32c, and 33c on the diffuser 34. Each of the arrows illustrates the intensity of the light that is diffused in the direction of the arrow.

Illumination light 31a, 32a, and 33a that are included in the diffused light illuminate points 31b, 32b, and 33b on the surface of the object 4 to be inspected from substantially tangential directions, respectively.

If the secondary diffused light sources 31c, 32c, and 33c are provided, each of the illumination light 31a, 32a, and 33a that travels in a direction close to the tangential direction of the inspection surface 4a of the object 4 can be obtained. In other words, since the inspection surface 4a is illuminated with a light flux which has a tangential illumination component, and an adhering substance such as a foreign substance or a surface roughness can be easily detected.

According to the present exemplary embodiment, the light that is emitted from the light source 2 transmits through the prism member 1, converted into illumination light with a considerable amount of oblique components, and then emitted. Further, after the light is emitted from the prism member 1, the light that is inclined with respect to a direction perpendicular to the inspection surface 4a is reflected by the reflection member 3, and then directed onto the object 4. This contributes to realizing an efficient illumination system. Further, the light that is emitted from the prism member 1 is reflected and diffused by the diffuser 34 which is provided on the opposite side of the light source 2, and the diffused light, which is the diffused light 35a, illuminates the inspection surface 4a.

According to the present exemplary embodiment, two types of illumination light which are the light that directly illuminates the object 4 after it is emitted from the prism member 1 and also the light that is emitted from the secondary diffused light source 33 are simultaneously incident on the object 4.

According to the present exemplary embodiment, the object 4 is illuminated with illumination light that includes light fluxes having a considerable amount of oblique components. Then, an image of the illuminated inspection surface 4a of the object 4 is taken by the camera 5.

According to the above-described configuration, a surface of a three-dimensional object can be uniformly illuminated with light at a large incident angle. This allows highly accurate detection of various surface defects such as a flaw or surface roughness on the surface of the object regardless of structure of the surface. Thus an illumination apparatus that is capable of illuminating an object under good lighting condition can be realized. By employing this illumination apparatus, an appearance inspection apparatus that allows highly precise visual inspection can be realized.

Figure 9:
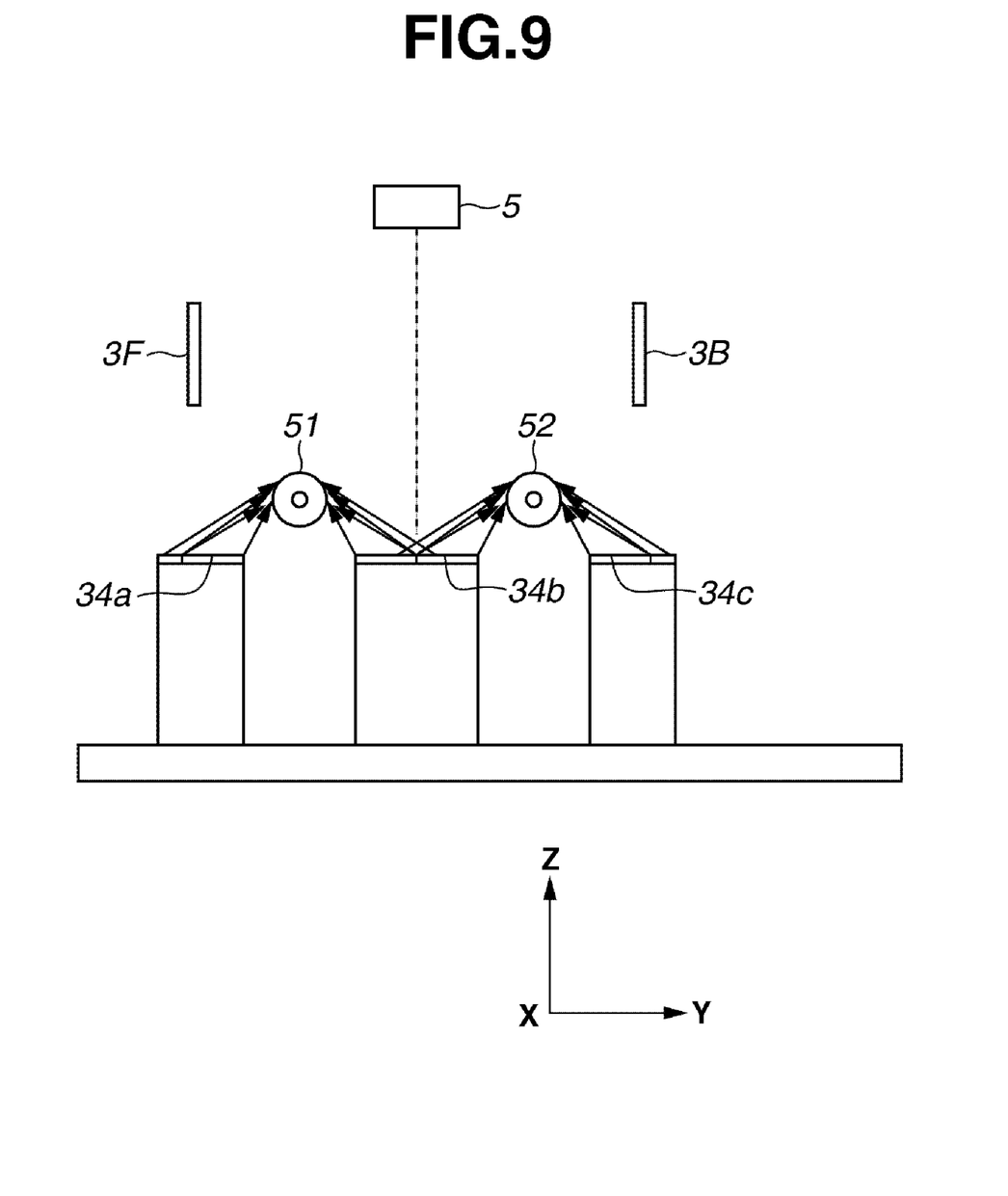
FIG. 9 is a front view of a main portion of an appearance inspection apparatus according to a second exemplary embodiment of the present invention.

FIG. 9 is a front view of a main portion of the appearance inspection apparatus in the vicinity of objects to be inspected according to a second exemplary embodiment of the present invention.

In FIG. 9, two objects 51 and 52 to be inspected are arranged in parallel to the X-axis. Diffusers 34a, 34b, and 34c are arranged in lower positions with respect to the objects 51 and 52 so that they are on both sides of the objects 51 and 52 when it is viewed from the camera 5. The diffusers 34a, 34b, and 34c are sheet type diffusers (diffusion sheets).

Figure 10:
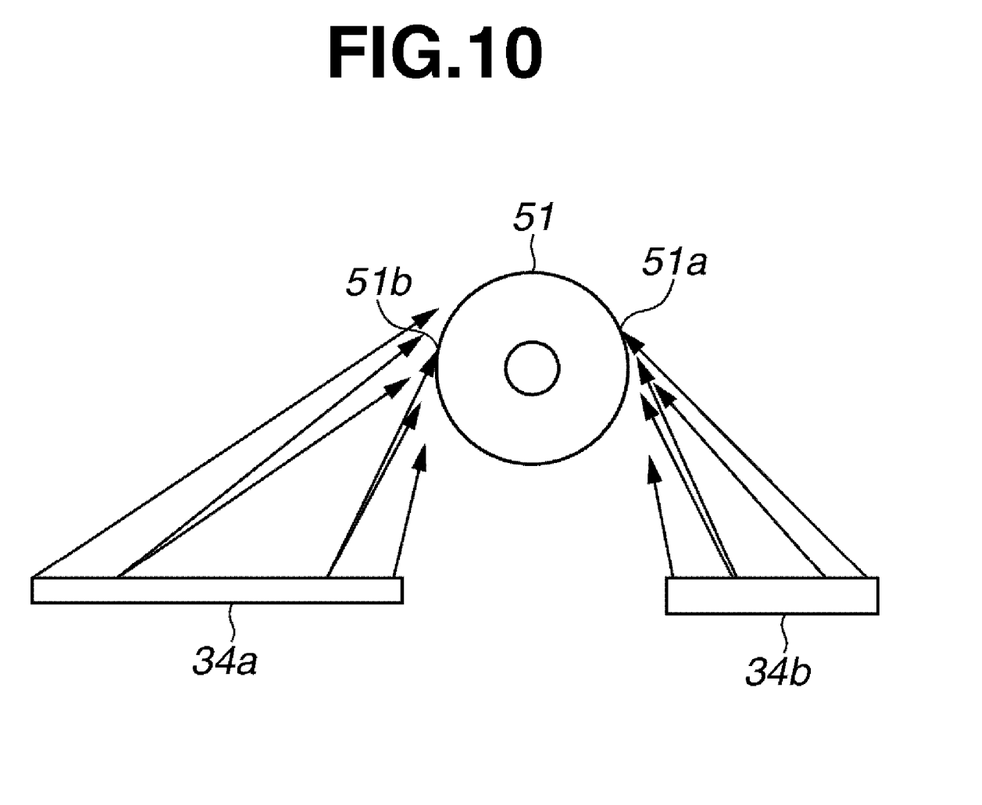
FIG. 10 illustrates an optical path of the secondary diffused light source illustrated in FIG. 9.

FIG. 10 illustrates optical paths of the diffused light that is emitted from secondary diffused light sources of the diffusers 34a and 34b and is incident on the object 51.

The diffused light illuminates inspection surfaces 51a and 51b which are provided on both sides of the object 51 under an illumination condition that is close to tangential illumination.

Figure 11:
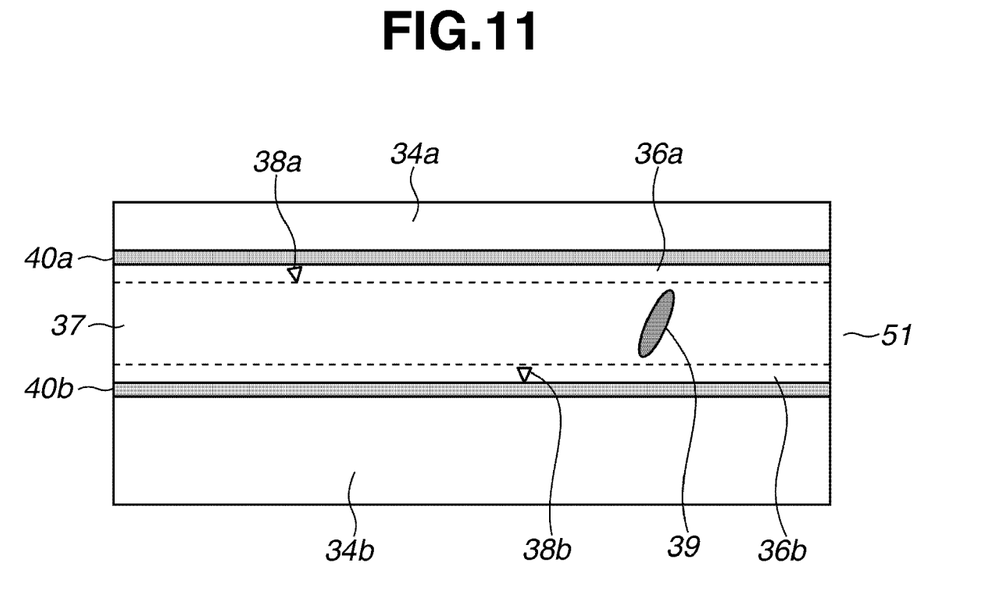
FIG. 11 illustrates an image of an object to be inspected which is photographed from above according to the second exemplary embodiment of the present invention.

FIG. 11 illustrates an image of the object 51 that is illuminated with the above-described illumination and taken by the camera 5. A similar image can also be taken according to the first exemplary embodiment. In FIG. 11, the object 51 is in the central portion, and the diffusers (diffusion sheets) 34a and 34b are provided on its upper and lower sides, respectively.

The object 51 is divided into two types of illumination areas. One is a central portion (central area) 37 that is illuminated with light that is emitted from the prism member 1 and has a considerable amount of oblique components. The other is an area that is illuminated with a light from the secondary diffused light sources. This area includes an area 36a which is on the upper side of the object 51 and an area 36b on the lower side. Light diffused by the diffusers 34a and 34b is directed onto the areas 36a and 36b. The areas 36a and 36b are illuminated under an illumination condition that is close to tangential illumination.

The image of the objects 51 and 52 are simultaneously taken while they are illuminated with different types of illumination depending on the areas as described above. In the central area 37, a defect 39 which is due to the degree of unevenness caused by a distribution of surface dents and projections is detected. In the areas 36a and 36b, adhering substances (foreign substances or surface roughness) 38a and 38b are detected.

Figure 12:
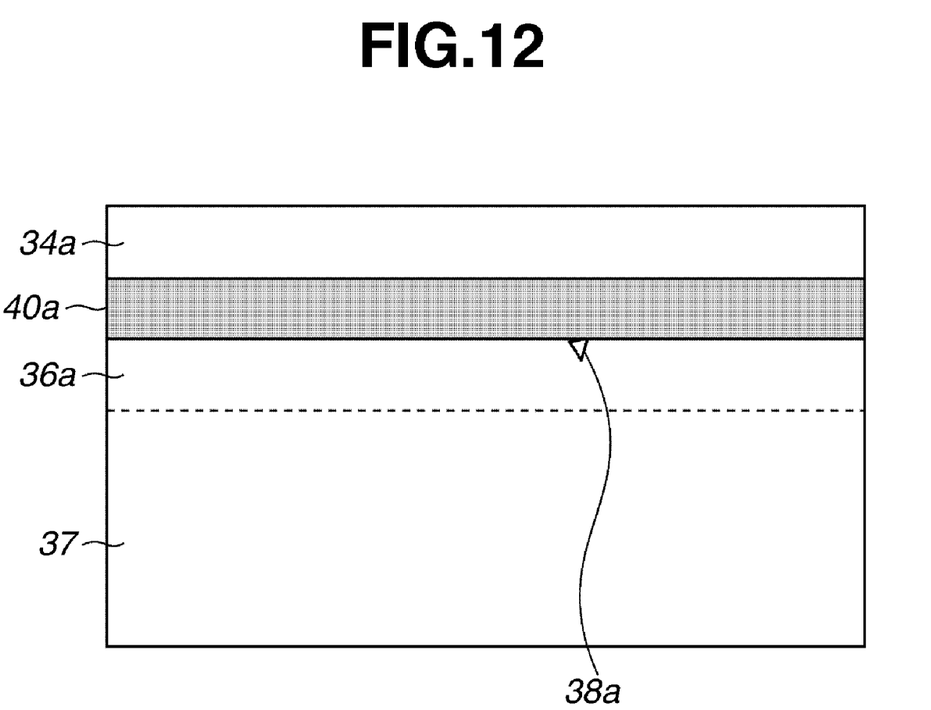
FIG. 12 is an enlarged view of the image illustrated in FIG. 11.

FIG. 12 is an enlarged view of the area 36a that is illustrated in FIG. 11 and includes the surface roughness 38a. The surface roughness 38a may be slightly raised from the surface of the object 51. If the surface roughness 38a is formed near an edge of the object 51, it is useful to set the background light darker. In this way, the image can be taken with increased contrast.

When seen from the imaging direction, it is useful to arrange the diffusers 34a and 34b so that small gaps 40a and 40b are formed between the diffusers 34a and 34b and the object 51 respectively.

The above-described image can also be obtained according to the first exemplary embodiment and used for the appearance inspection of the inspection surface as is with the second exemplary embodiment.

Figure 13:
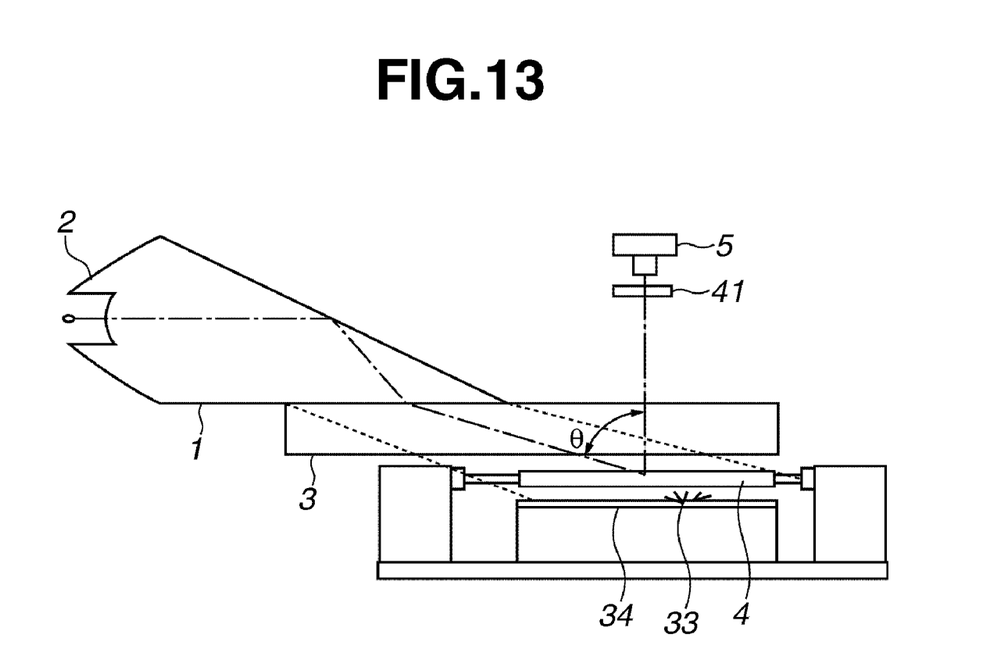
FIG. 13 illustrates a configuration of the whole apparatus or a lateral view of an apparatus according to a third exemplary embodiment of the present invention.

FIG. 13 is a lateral view of an overall configuration of the appearance inspection apparatus according to a third exemplary embodiment of the present invention. According to the present exemplary embodiment, illumination using light which has a considerable amount of oblique components is realized by the prism member 1, and the image is taken from a substantially vertical direction with respect to the surface of the object 4 to be inspected as is with the first exemplary embodiment.

Figure 15:
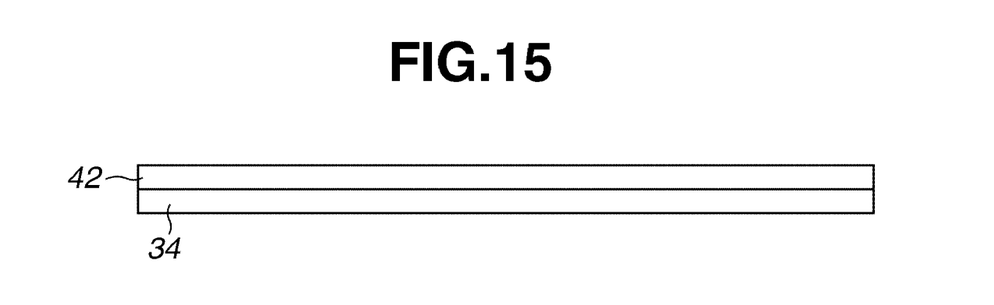
FIG. 15 illustrates a part of a configuration of a diffuser and a polarizer sheet.

The difference between the third and the first exemplary embodiments is that, as illustrated in FIG. 15, a first polarizer 42 that emits linear polarized light is provided on the surface of the diffuser 34 on its light-incident side in the third exemplary embodiment.

Further, a second polarizer 41 that also emits linear polarized light is provided in the imaging optical path (in front) of the camera 5. The first polarizer 42 and the second polarizer 41 are arranged such that they are in crossed nicols (planes for polarized light are at right angles).

Figure 14:
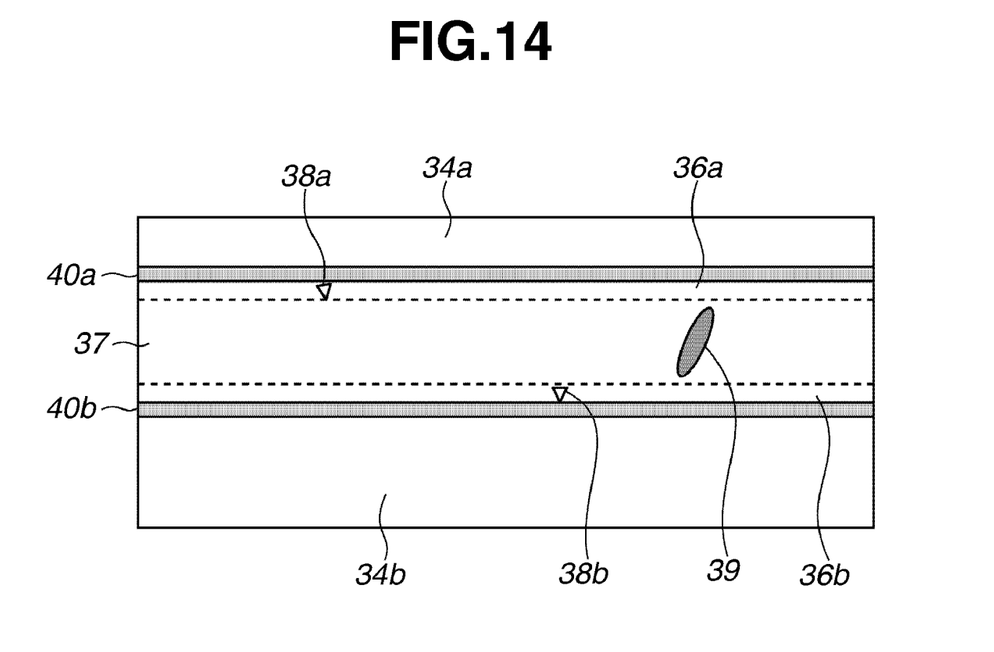
FIG. 14 illustrates an image photographed by the appearance inspection apparatus according to the third exemplary embodiment of the present invention.

Light that is scattered by a foreign substance or surface roughness is incident on the camera 5 with its polarization state changed. According to the present exemplary embodiment, an image with an emphasized foreign substance or surface roughness can be obtained by providing the two polarizers. FIG. 14 illustrates an image obtained in this manner.

The image of the central area 37 of the object 4 is taken using unpolarized illumination. Since this image is similar to an image that is taken without using a polarized plate, unevenness on the surface caused by distribution of surface dents and projections can be detected.

An ideal image of the central area 37 and its peripheral areas 36a and 36b can be obtained by balancing the light quantity at the central area 37 and the peripheral areas 36a and 36b and suitably setting reflectance of the diffusers 34a and 34b.

According to the exemplary embodiments of the present invention, an adhering substance on the inspection surface 4a of the object 4 can be detected with increased accuracy by the above-described configurations.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-284223 filed Nov. 5, 2008, which is hereby incorporated by reference herein in its entirety.

What is claimed is:

1. An illumination apparatus which illuminates a surface of an object having a three-dimensional shape, the illumination apparatus comprising:
   a light source;
   a guide configured to guide light from the light source to a surface of the object; and
   a diffuser which has a diffusion-reflection surface that faces a light exit surface of the guide via the object;
   wherein the diffuser is arranged at such a position that the light which is emitted from the guide and is not directly incident on the object is incident on the diffusion-reflection surface while a part of the light reflected and diffused by the diffusion-reflection surface is incident on a surface of the object, and
   wherein the object is a cylindrical object, and the guide is configured to illuminate a cylindrical surface of the cylindrical object from an oblique direction with respect to its normal line with rectangular light that is long in a direction parallel to a cylinder axis of the cylindrical object.

2. The illumination apparatus according to claim 1, further comprising:
   a reflection member arranged between the guide and the object,
   wherein the reflection member includes a pair of reflection surfaces that are arranged to face each other, and the reflection member reflects, among the light that is emitted from the guide, light that does not directly illuminate the object to the direction of the object.

3. The illumination apparatus according to claim 2, wherein the object is a cylindrical object, and wherein the pair of reflection surfaces of the reflection member are arranged along a direction of a cylinder axis of the cylindrical object so as to face each other.

4. The illumination apparatus according to claim 1, wherein the guide includes a prism member, wherein the prism member includes a first light incident surface, a second light incident surface, and a third light incident surface, each of which a portion of the light emitted from the light source is incident on, a first reflection surface that reflects the light incident on the first light incident surface, a second reflection surface that reflects the light incident on the second light incident surface to a direction of the first reflection surface, and a third reflection surface that reflects the light incident on the third light incident surface to a direction of the first reflection surface; and an exit surface from which the light reflected by the first reflection surface is emitted.

5. An appearance inspection apparatus comprising:
an illumination apparatus according to claim 1, and
a camera configured to take an image of an object illuminated with light from the illumination apparatus.

6. The appearance inspection apparatus according to claim 5, further comprising:
a first polarizer which is arranged on an light incident side of the diffusion-reflection surface of the diffuser and configured to emit linear polarized light; and
a second polarizer which is arranged in an imaging optical path of the camera and configured to emit linear polarized light,
wherein the second polarizer is arranged to be in a relation of crossed nicols with the first polarizer.

* * * * *